United States Patent [19]
Bredesen

[11] Patent Number: 5,576,209
[45] Date of Patent: Nov. 19, 1996

[54] METHOD FOR INCREASING THE RESISTANCE OF NEURAL CELLS TO β-AMYLOID PEPTIDE TOXICITY

[75] Inventor: Dale E. Bredesen, Palos Verdes Estates, Calif.

[73] Assignee: The Regents of the University of California, Oakland, Calif.

[21] Appl. No.: 328,581

[22] Filed: Oct. 24, 1994

[51] Int. Cl.⁶ .............................. C12N 5/06; C12N 5/08; A61K 38/18

[52] U.S. Cl. .................................... 435/240.2; 435/240.1; 435/240.21; 514/2; 514/12

[58] Field of Search .............................. 435/240.1, 240.2, 435/240.21, 4, 7.1, 7.2; 514/2, 12, 44; 536/24.1

[56] References Cited

FOREIGN PATENT DOCUMENTS 9005138  5/1990  WIPO.

OTHER PUBLICATIONS

Rabizadeh et al., "Induction of Apoptosis by the Low–Affinity NGF Receptor," Science, 16 Jul. 1993, vol. 261, pp. 345–348.
Takadera et al., Neurosci. Lett., vol. 161, pp. 41–44, 1993.
Kozlowski et al, J. Neurosci., vol. 12, pp. 1679–1687, 1992.
Yankner et al., PNAS USA, vol. 87, pp. 9020–9023, 1990.
Mattson et al., Brain Res., vol. 621, pp. 35–49, 1993.

Primary Examiner—Stephen G. Walsh
Assistant Examiner—Stephen Gucker
Attorney, Agent, or Firm—Poms, Smith, Lande & Rose

[57] ABSTRACT

Neural cells which express P75 nerve growth factor receptor ($p75^{NTR}$) and which have a low resistance to β-amyloid peptide toxicity are treated with a binding agent that binds with $p75^{NTR}$. The resulting neural cells display an increased resistance to β-amyloid peptide toxicity. Mutant and transfected neural cells are also disclosed in which the ability to express $p75^{NTR}$ has been removed with a resultant increase in resistance to β-amyloid peptide toxicity.

4 Claims, 1 Drawing Sheet

METHOD FOR INCREASING THE RESISTANCE OF NEURAL CELLS TO β-AMYLOID PEPTIDE TOXICITY

This invention was made with support under Grant Number AG10671 from the National Institute of Health. Accordingly, the U.S. Government has certain rights in the invention.

BACKGROUND OF THE INVENTION

1. Field of the Invention

The present invention relates generally to β-amyloid peptide and its toxic effects with respect to neural cells. More particularly, the present invention relates to neural cells which express low-affinity nerve growth factor receptor and methods for increasing the resistance of such cells to β-amyloid peptide toxicity.

2. Description of Related Art

The publications and other reference materials referred to herein to describe the background of the invention and to provide additional detail regarding its practice are hereby incorporated by reference. For convenience, the reference materials are numerically referenced and grouped in the appended bibliography.

A hallmark of Alzheimer disease is an early and severe telencephalic cholinergic deficit preferentially involving temporal lobe and limic cortical structures, hippocampus, and amygdala (1–3). The degree of cholinergic decrement correlates well with the severity of dementia (3). Decreases in other neurotransmitters occur to a lesser extent (3), and such deficits are not proportional to the magnitude of intellectual impairment (4).

Virtually all of the cholinergic innervation of the outer cerebral mantle derives from the basal nuclear complex, which is composed of the medial spetal nucleus, nuclei of the diagonal band, magnocellular preoptic area, ventral pallidum/substantial innominata region, nucleus basalis, and nucleus of the ansa lenticularis (5–7). This constellation of cholinergic neutrons undergoes degeneration in Alzheimer disease and in at least 13 other diseases in which dementia features prominently (8–10), leading to the question of what characteristic renders these cells selectively vulnerable in those conditions (8).

β-amyloid peptide (βAP) has been shown to be neurotoxic in primary neural cell cultures (11). Moreover, βAP has been implicated in the pathogenesis of Alzheimer disease by the discovery of mutations in the β-amyloid precursor protein gene in a small percentage of familial Alzheimer disease patients (12). In addition, the extent of neuronal loss in the basal forebrain of patients with Alzheimer disease is positively correlated with the degree of β-amyloid accumulation in that region (13).

However, the finding of βAP neurotoxicity does not explain the predisposition of the cholinergic neurons of the basal nuclear complex to degeneration in Alzheimer disease. These neurons express the highest levels of $p75^{NTR}$, the low-affinity nerve growth factor receptor (NTR), in the brain; in contrast, neurons of the other major cholinergic complex in the mammalian brain, the pedunculopontine and laterodorsal tegmental nuclei, neither express $p75^{NTR}$ nor undergo degeneration in Alzheimer disease (14, 15). $p75^{NTR}$ expression has been demonstrated to enhance apoptosis in the unbound state, whereas, when $p75^{NTR}$ is bound by nerve growth factor (NGF) or monoclonal antibody, cell survival is enhanced (16).

In view of the above, there is a continuing need to further investigate NTR and its relationship to β-amyloid peptide toxicity with respect to neural cells involved in Alzheimer disease.

SUMMARY OF THE INVENTION

In accordance with the present invention, it was discovered that there is a direct functional relationship between the expression of p75 nerve growth factor receptor $p75^{NTR}$ by neural cells and the toxicity of β-amyloid peptide with respect to such cells. Neural cells which express $p75^{NTR}$ are easily attacked by β-amyloid peptide. Whereas, neural cells in which $p75^{NTR}$ is bound by NGF or monoclonal antibodies demonstrate increased resistance to the toxic effects of β-amyloid peptide.

As a feature of the present invention, a method is provided for increasing the resistance of neural cells to β-amyloid peptide toxicity where the neural cells naturally express the $p75^{NTR}$ and have a low resistance to β-amyloid peptide toxicity. The method involves treating the neural cells with a binding agent, such as NGF or monoclonal antibody, in an amount which is sufficient to bind the $p75^{NTR}$ which are naturally expressed by the cells. A modified neural cell culture is formed in which $p75^{NTR}$ is bound by the binding agent. The modified neural cells are then exposed to β-amyloid peptide to demonstrate their increased resistance to degeneration.

Methods in accordance with the present invention are well-suited for use in investigating the toxic effects of β-amyloid peptide on neural cells, such as basal forebrain cholinergic neurons, which naturally express relatively large amounts of $p75^{NTR}$. The investigative methods involve providing an in vitro neural cell culture which includes a plurality of neural cells which naturally express p75 growth factor receptor and which have a low resistance to β-amyloid peptide toxicity. The neural cell culture is treated with a binding agent in an amount sufficient to bind $p75^{NTR}$ which is naturally expressed by the cells. The resulting modified cells culture is exposed to β-amyloid peptide and the toxic effects of the exposure measured.

The above basic investigative method can be used alone or in combination with a wide variety of other cell treatment protocols to assess the relative merits of a particular protocol with respect to enhancing neural cell resistance to β-amyloid peptide toxicity and possible treatment regiments for Alzheimer disease.

As another feature of the present invention, the resistance of neural cells to β-amyloid peptide toxicity can be increased by genetically altering the neural cell to eliminate the expression of $p75^{NTR}$. This alternative method may be used in treatment protocols to increase neural cell resistance to β-amyloid peptide toxicity and in methods designed to investigate the relationship between β-amyloid peptide, neural cells and Alzheimer disease.

The above discussed and many other features and attendant advantages of the present invention will become better understood by reference to the following detailed description when taken in conjunction with the accompanying drawings.

DETAILED DESCRIPTION OF THE PREFERRED EMBODIMENTS

Figure 1:
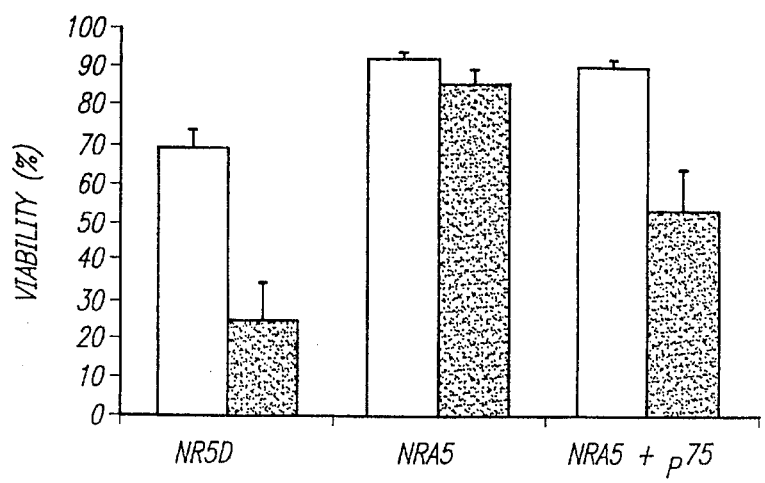
FIG. 1 is a bar graph showing the results of tests which demonstrate that cellular resistance to attack by β-amyloid peptide is increased when $75^{NTR}$ is not expressed by a neural cell population.

The present invention involves a method for increasing the resistance of neural cells to β-amyloid peptide toxicity. The method is applicable to neural cells which express $p75^{NTR}$ and which are not resistant to β-amyloid peptide toxicity. Exemplary neural cells include basal forebrain cholinergic neurons, cortical neurons, hippocampal neurons, nucleus basalis neurons, and neurons in which $p75^{NTR}$ has been upregulated due to axotomy or other insult. Cortical neurons do not express $p75^{NTR}$ in the normal adult brain. However, cortical neurons do express $p75^{NTR}$ in temporal association with degeneration, both during development (23) and in Alzheimer disease (24). Hippocampal neurons express $p75^{NTR}$ when primary cultures are exposed to β-amyloid peptide (22). The method of the present invention may not be applicable to neural cells such as Purkinje cells. Purkinje cells express relatively high levels of $p75^{NTR}$ (25) but are not prone to degeneration in Alzheimer disease. This may be because the cerebellum does not develop congophilic β-amyloid deposits during the course of Alzheimer disease (26); alternatively, Purkinje cells may differ from neurons of the basal nuclear complex in the expression of another gene or genes that inhibit $p75^{NTR}$-mediated neural cell death, as the expression of bcl-2 does in PC12 cells (18). The method basically involves treating or modifying the neural cells to eliminate $75^{NTR}$ with the result being an increase in the cells ability to resist β-amyloid peptide toxicity.

The above neural cells can be treated or modified in accordance with the present invention in either an in vitro or in vivo environment. In one embodiment, a binding agent which is specific for $p75^{NTR}$ is added to the cell population. The binding agent binds to and inactivates the p75 receptor with a resultant increase in the cell cultures resistance to β-amyloid peptide toxicity. In a second embodiment of the present invention, the neural cell population which naturally expressed $p75^{NTR}$ is genetically modified so that $p75^{NTR}$ is no longer expressed. The resulting modified cell population which is free of $p75^{NTR}$ displays an increased resistance to β-amyloid peptide toxicity.

With respect to the first embodiment, the neural cells are treated by direction application of a binding agent to the neural cell culture in vitro. The binding agent specifically binds to the $p75^{NTR}$. Suitable binding agents include nerve growth factor (NGF) or monoclonal antibodies which are known to bind specifically with $p75^{NTR}$. Exemplary monoclonal antibodies include monoclonal antibody 192; other neurotrophins binding $p75^{NTR}$ include BDNF, NT-3 and NT-4/S.

The amount of binding agent which must be added to the cull culture in order to achieve required levels of $p75^{NTR}$ binding will vary depending upon the culture conditions, cell type, number of cells and specific binding agent. The various parameters are easily established by routine experimentation. For Example, one can determine when a sufficient amount of binding agent has been added to the neural cell culture by adding differing amounts of the binding agent to cell cultures and measuring the increase in the modified cell cultures resistance to β-amyloid peptide toxicity. Typically, the amount of binding agent which is added to the cell culture is sufficient to provide a concentration in the cell growth media on the order of 2 nM–50 nM, depending on the neurotrophin used (10 μg/ml for monoclonal antibody). NGF, available from a number of commercial sources and may also be isolated according to the procedure descried in Mobley et al., 1976 (Biochem. 1976; 15:5543–5552). Monoclonal antibodies which are specific to $p75^{NTR}$ are also available from a number of commercial sources, such as Boehringer-Mannheim, Inc. The monoclonal antibodies may also be prepared, if desired, according to the procedure set forth in Chandler et al., 1984 (J. Biol. Chem. 1984; 259:6882–6889).

When carrying out the above method in vitro, the treatment step involves adding the binding agent directly to the cell culture media. Addition of the binding agent is carried out according to well-known procedures for adding chemical agents to cell cultures. The cell cultures themselves are grown and maintained in accordance with conventional cell growth protocols. Within a few hours after treatment with the binding agent, β-amyloid peptide may be added to the cell culture and the increase in cellular resistance to toxicity observed. The concentration of β-amyloid peptide in the growth media which is typically necessary to cause cell death ranges from 0.5 μM to 100 μM.

When used to enhance neural cell resistance to β-amyloid peptide toxicity in vivo, the binding agent must be combined with a suitable pharmaceutical carrier and introduced into the animal. Suitable pharmaceutical carriers include saline, or buffered salt solutions (with or without added nutrients). Preferably, the binding agent and pharmaceutical carrier are injected intracerebrally for transport to neural cells (or expressed by transplanted cells). Dosages adequate to maintain concentrations of 5–50 nM are required: on the order of 1 μg to 10 μg binding agent per kilogram body weight. However, dosage levels and frequency of injections will vary depending upon the particular patient and other factors including the extent of existing neural cell damage. Intraventricular administration via pump may be used. Alternatively, intravenous or subcutaneous injection of 5 mg/kg daily may be employed.

In addition to being useful in enhancing resistance to β-amyloid toxicity, the present invention provides a method for investigating the toxic effects of β-amyloid peptide on neural cells. The investigative method involves the same initial step of adding the binding agent to a number of cell cultures. Then, the cell cultures are exposed to varying amounts of β-amyloid peptide for periods ranging up to a few days. The extent of cell viability is then measured. As part of an overall investigative procedure, various different drugs may be administered to the cell cultures during exposure to β-amyloid peptide in order to study the effect of such drugs on cell viability. Various treatment protocols may also be carried out on the cell cultures during exposure to β-amyloid in order to investigate their effect on cell viability.

In the alternate embodiment of the present invention, the expression of the $p75^{NTR}$ is eliminated by genetically modifying the neural cell rather than binding the expressed receptor. Any of the conventional procedures for genetically altering the neural cells by mutation or by introduction of cDNA to prevent expression of the $p75^{NTR}$ without otherwise adversely affecting the cell may be used. These conventional procedures for preparing modified neural cells or cell mutants which lack the ability to express $p75^{NTR}$ are well-known to those of ordinary skill in the art. For example, mutant neural cells which do not express $p75^{NTR}$ may be prepared by PC12 cells maintained in Dulbecco's minimum essential medium (DMEM; Gibco) containing 5% horse serum and 5% supplemented cell serum (Hyclone), in 12% $CO_2$ at 37° C. Cells were mutagenized with 10 mM ethyl methanesulfonate for 6 hours and then washed with 2×10 ml of medium. After growing for 10 days, cells were trypsinized and subcultured into 36 plates at an approximate density of $10^4$ cells per plate. The cells were grown for 10 days (approximately five division) and then treated with NGF (25 ng/ml) for 5 days. Groups of clonally derived cells that did not respond to NGF by extending neurites were isolated, subcloned, and then treated for the absence of NGF-induced neurite outgrowth and the presence (or absence) of $P75^{NTR}$ by Northern (RNA) and protein immunoblot analysis. The two subclones used in these experiments were the NRA5 subclone, which does not express $p75^{NTR}$, and NR5D, which does express $p75^{NTR}$.

The mutant or modified neural cells which no longer express $p75^{NTR}$ are then exposed to β-amyloid peptide and their increased resistance to toxicity measured. The mutant or modified neural cell may be used to investigate the mechanisms of interactions between β-amyloid peptide and neural cells as they relate to Alzheimer disease.

Examples of practice are as follows:

EXAMPLE 1

PC12 Pheochromocytoma Cell Mutants Which Do Not Express $p75^{NTR}$ Have Increased Resistance to β-Amyloid Peptide Toxicity In the following example, the effectiveness of the present invention in increasing the resistance of the PC12 neural cell line to β-amyloid peptide toxicity is demonstrated. PC12 is a common neural cell line which is known to naturally express the $p75^{NTR}$. PC12 cells are available commercially from American Type Culture Collection (Bethesda).

PC12 cells were maintained in Dulbecco's minimum essential medium (DMEM Gibco) containing 5% horse serum and 5% supplemental calf serum (Hyclone) in 12% $CO_2$ at 37° C. Cells were mutagenized with 10 mM ethyl methanesulfonate for 5 hours and then washed with 2×10 ml of medium. After growing for 10 days, cells were trypsinized and subcultured into 36 plates at an approximate density of $10^4$ cells per plate. The cells were grown for 10 days (approximately 5 divisions) and then treated with NGF (25 ng/ml) for 5 days. Groups of clonally derived cells that did not respond to NGF by extending neurites were isolated, subcloned and then tested for the absence of NGF-induced neurite outgrowth and the presence (or absence) of $p75^{NTR}$ by Northern (RNA) and protein immunoblot analysis. The two subclones used in this example were isolated as the NRA5 subclone which did not express $p75^{NTR}$ and the NR5D subclone which did express $p75^{NTR}$.

Expression of $p75^{NTR}$ in PC12 and PC12 mutant cells were determined by flow cytometry using monoclonal antibody 192 (1:100 dilution) as primary antibody and fluorescein-labeled goat anti-mouse IgG+IgM (Kirkegaard & Perry Laboratories) as secondary antibody.

Cell cultures of the two PC12 mutants were exposed to 50 μM β-amyloid peptide for 3 days to determine the relative resistance of the cultures to β-amyloid peptide toxicity. The results of the testing are shown in FIG. 1. The open bars represent cell culture viability when no β-amyloid peptide was added. The solid bars depict cell culture viability when β-amyloid peptide was added. As shown in FIG. 1, the mutant NR5D, which expressed the $p75^{NTR}$, was susceptible to attack by β-amyloid peptide. In contrast, the mutant NRA5, which did not express the p75 receptor, displayed increased resistance to β-amyloid peptide toxicity.

In order to further confirm the relationship between $p75^{NTR}$ expression and β-amyloid peptide toxicity, the NRA5 mutant was transfected with an expression vector which provided the NRA5 mutant with the ability to express $p75^{NTR}$.

The NRA5 mutant which expressed p75 receptor was prepared as follows:

The $p75^{NTR}$ cDNA to pUC9 was digested with Sal I, filled in with Klenow fragment and deoxynucleotide triphosphates, and then digested with Bgl II. The 1.7-kb fragment containing the entire open reading frame of $p75^{NTR}$ was then ligated into PUC18 that had been digested with Sma I and Bam HI. The resulting plasmid was digested with Ecc 47III and Sal I and ligated into pBabepuro (27) that had been cut with Sna BI and Sal I to create pBabe-puro-$p75^{NTR}$. PC12 NRA5 cells were transfected with pBabe-puro and pBabe-puro-$p75^{NTR}$ by using the cationic lipid N-[1-(2,3-diolcoyloxy)propyl]-N,N,N-trimethylammonium methyl sulfate (DOTAP, Boehringer Mannheim) according to the supplier protocol. Stably transfected cells were selected in puromycin (10 μg/ml). Pools containing >100 stably transfected colonies were used rather than single colonies, to avoid the bias inherent in comparing single colonies (16).

Viability of these NRA5 cells in which expression of $p75^{NTR}$ was restored was determined in serum-free medium and βAP (25–50 μM) was used to make the determination. The βAP fragment βAP-(1–40), obtained from Athena Neurosciences (San Francisco), was dissolved in sterile tissue culture (Mediatech, Herndon, Va.) at a concentration of 1 mM and further diluted in serum-free medium. Preincubation at 37° C. for 48 hours was carried out prior to use of the peptide, except from one synthesis of βAP, in which preincubation was demonstrated to lead to reduced toxicity on primary neuronal cultures.

The results of these tests are shown graphically in FIG. 1 (NRA5+p75). The open bar shows cell viability in serum free media and the solid bar shows cell viability when β-amyloid peptide was added. As can be seen from FIG. 1, the NRA5 cell line became susceptible to β-amyloid peptide toxicity when it was modified to express $p75^{NTR}$.

EXAMPLE 2

Figure 2:
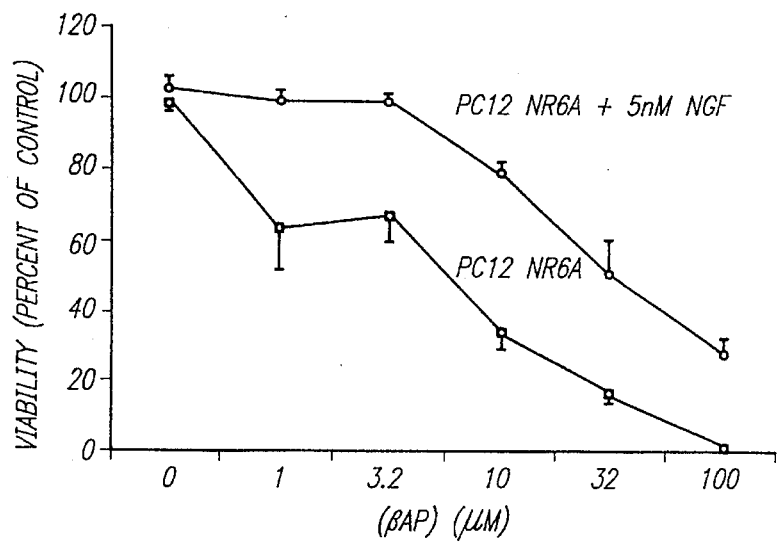
FIG. 2 is a graph of test results showing that addition of a binding agent (NGF) to a neural cell line which expresses $p75^{NTR}$ increases the cell lines resistance to attack by β-amyloid peptide.

Treatment with NGF Increases Resistance of PC12 Cell Line to β-Amyloid Peptide Toxicity A third mutant cell line (NR6A) was prepared in the same manner as the NR5A cells described above. The NR6A cells expressed $p75^{NTR}$, but did not express TrkA which is the known high affinity nerve growth factor receptor. The effect of β-amyloid toxicity on this cell line was determined both before and after the addition of NGF as a binding agent. The results of these tests are summarized in FIG. 2. As shown in FIG. 2, the NR6A cells were sensitive to β-amyloid toxicity with a $LD_{50}$ of approximately 5 μM with the $LD_{50}$ increasing to approximately 50 μM when 5 nM NGF was added. Mutant NGF (K32A, K34A and E35A) was also added in amounts of 5 nM to NR6A cells. These mutant NGF are known to bind TrkA, but not $p75^{NTR}$ (21). Addition of these types of NGF had no effect on the resistance of NR6A to β-amyloid peptide toxicity. This further confirms that the observed increase in resistance to β-amyloid peptide toxicity is due to binding of the p75 receptor.

Figure 3:
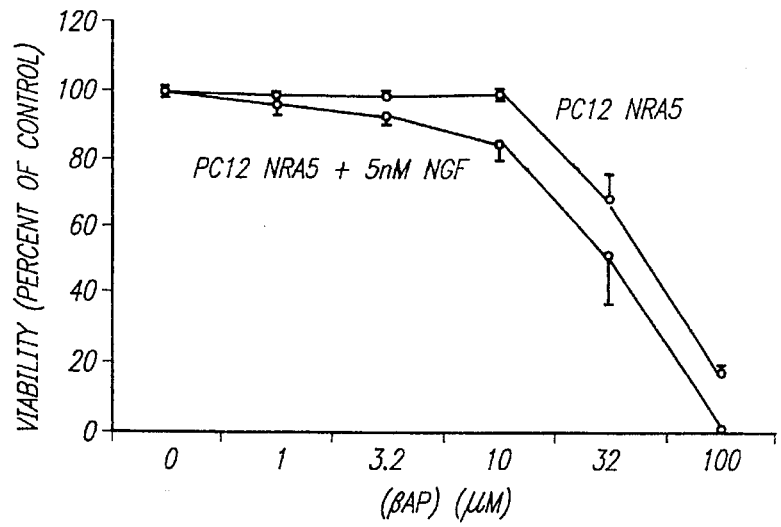
FIG. 3 is a graph of test results showing that addition of a binding agent (NGF) to a modified neural cell line which does not express $p75^{NTR}$ has little effect on cell viability.

NGF was added to NRA5 cells to further confirm that the observed enhancement in resistance to β-amyloid peptide toxicity was due to NGF binding of the p75 receptor. The NRA5 cells did not express p75 receptor but they did express TrkA. The addition of NGF to the NRA5 cells showed no increase in cell resistance to β-amyloid peptide toxicity. Instead, a slight decrease in resistance was noted. The results of these tests are shown in FIG. 3.

EXAMPLE 3

Removal of p75 Receptor Expression from CSM14.1 Cell Line Increases Resistance to β-Amyloid Peptide Toxicity CSM 14.1 cells (20) are rat nigral neural cells immortalized with the temperature-sensitive large T antigen of SV40. These cells express tyrosine hydroxylase, neuron-specific enolase, and neurofilament (NF-L). CSM 14.1 cells were transfected with pBabe-puro-p75$^{NTR}$ with the cationic lipid DOTAP (Boehringer Mannheim, Inc.) and then selected in puromycin (7 µg/ml). The comparison of single colonies can introduce bias into the results (28) but this was obviated by comparison of entire pools of stable transfectants (28). Therefore pools of stable transfectants populations including more than 100 separate colonies, with pBabe-puro-p75$^{NTR}$ were compared with pools of pBabe-puro transfectants. Cells were grown in DMEM with fetal povine serum (FBS) 10%) at 34° C. in 5% $CO_2$. Total RNA was prepared by the method of Chomczynski (29), and electrophoresis was carried out in formaldehyde gels. After Northern transfer to nylon, $^{32}$P-labeled probes for p75$^{NTR}$. 0.1 b cDNA fragment digested with Stu I) Trk, 0.5 b cDNA fragment digested with XncI and viactin were hybridized sequentially. Blots were exposed to film for 24 hours for the p75$^{NTR}$ and Trk A probes and for 2 hours for the viactin probe. For immunocytochemistry, cells were fixed in paraformaldehyde (4%) for 15 minutes and permeabilized in 0.1% Triton X-100. Immunocytochemistry was done as described (18), with a polyclonal antibody (1–2500) to purified p75$^{NTR}$. As controls, primary antibody was omitted and control transfectants were stained, both of these controls showed a similar lack of staining.

After transfection with pBabe-puro or pBabe-puro-p75$^{NTR}$, p75$^{NTR}$ expression in CSM14.1 was assessed by immunocytochemistry with monoclonal antibody 192 as primary antibody as described (16). The CMSM14.1 transfectants which expressed p75$^{NTR}$ displayed the same susceptibility to attack by β-amyloid peptide as the NR5 D PC12 mutant. The CSM14.1 transfectant which did not express p75$^{NTR}$ had a much higher resistance to β-amyloid peptide toxicity. This is a further example which shows the direct functional relationship between the presence of p75$^{NTR}$ in a neural cell population and the cell population's resistance to β-amyloid peptide toxicity.

EXAMPLE 4

Binding of p75$^{NTR}$ in Nucleus Basalis Neurons to Increase Resistance to β-Amyloid Peptide Toxicity Cell cultures of nucleus basalis neurons are prepared and maintained according to convention protocols as follows: Basal forebrain of E12-E19 rat is dissected, triturated and placed on poly-lysine coated plates, and fed with Dulbecco's modified minimum essential medium at 10% FB5 (alternatively, monoclonal antibody 192, 10 µg/ml).

The cell cultures are treated with a sufficient amount of NGF to provide culture medias having an NGF concentration of 5 nM. Twenty-four hours after NGF addition, β-amyloid peptide is added in varying amounts to the different cultures and cell viability is measured at 12-hour intervals for 3 days.

EXAMPLE 5

In Vivo Studies

β-amyloid 10 µg/ml, 1/14 5 µl is injected into the brain (basal forebrain). Prior to injection of β-amyloid (by 24 hours), monoclonal 192 (50 µg/ml, 10 µl) or BDNF (50 nM) is injected into the same region. After 7 days, animals are sonified and neuronal viability determined by regional cell counts or immunohistochemistry.

Having thus described exemplary embodiments of the present invention, it should be noted by those skilled in the art that the disclosures herein are exemplary only and that various other alternations, adaptations and modifications may be made within the scope of the present invention. Accordingly, the present invention is not limited to the specific embodiments as illustrated herein.

BIBLIOGRAPHY

1. Brun, A. and Gustafson, L. (1976) *Arch. Psychiatr. Nervenkr.* 223, 15–33.
2. Davies, P. and Maloney, A. J. (1976) *Lancet* ii, 1403.
3. Bowen, D. M. & Davidson, A. N. (1986) *Br. Med. Bull.* 42, 75–80.
4. Francis, P. T. *** (1985) *N. Engl. J. Med.* 313, 7.11.
5. Bigl, V. Woolf, N. J. and Butcher, L. L. (1982), *Brain Res. Bull.* 8, 727–749.
6. Woolf, N. G., Hermit, M. C. and Butcher, L. L. (1986), *Neurosci. Lett.* 66, 281–286.
7. Butcher, L. L. and Semba, K. (1989), *Trends Neurosci.* 12, 483–485.
8. Averback, P. (1981) *Arch. Neurol.* 38, 230–235.
9. Cummings, J. L. and Benson, D. F. (1987) *Alzheimer Dis. Assoc. Disord.* 1, 128–155.
10. Bigl, V. Arendt, T. and Biesold, D. (1990) in *Brain Cholinergic Systems,* eds. Sterlade, M. and Biesold, D. (Oxford Univ. Press, Oxford), pp. 364–386.
11. Yankner, B. Duffy, L. and Kirschner, D. (1990) *Science* 250, 279–282.
12. Goate, A. Chartier-Harlin, M.-C., Mullan, M., Brown, J. Crawford, F., Fidani, L., et al. (1991) *Nature (London)* 349, 704–706.
13. Arendt, T., Taubert, V., Bigl, V. and Arendt, A. (1988) *Acta Neuropathol.* 75, 226–232.
14. Woolf, N. J., Jacobs, R. W. and Butcher, L. L. (1989) *Neurosci. Lett.* 96, 277–282.
15. Woolf, N. J., Gould, E. and Butcher, L. L. (1989) *Neuroscience* 30, 143–152.
16. Rabizadeh, S., Oh, J., Zhong, L.-T., Yang, J., Bitler, C. M., Butcher, L. L. and Bredesen, D. E. (1993) *Science* 261, 345–348.
17. Liu, Y.-J., Joshua, D. E., Williams, G. T., Smith, C. A., Gordon, J. and MacLennan, I. C. M. (1989) *Nature (London)* 342, 929–931.
18. Mah, S. P. et al., *J. Neurochem.* 60, 1183–1186 (1993).
19. Behl, C., Davis, J., Cole, G. M. and Schubert, D. (1992) *Biochem. Biophys. Res. Commun.* 186, 944–950.

20. Durand, M., Chugani, D. C., Mahmoudi, M. and Phelps, M. E. (1990) *Soc. Neurosci Abstr.* 16, 40.
21. Ibañez, C. F., Ebendal, T., Barbany, G., Murray-Rust, J., Blundell, T. L. and Persson, H. (1992) *Cell* 69 329–341.
22. Yanker, B., Caceres, A. and Duffy, L. K. (1990) *Proc. Natl. Acad. Sci. USA* 87, 9020–9023.
23. Meinecke, D. L. and Rakie, P. (1993) *Neuroscience* 54, 105–116.
24. Mufson, E. J. and Kordower, J. H. (1992) *Proc. Natl. Acad. Sci. USA* 89, 569–573.
25. Mufson, E. J., Higgins, G. A. and Kordower, J. H. (1991) *J. Comp. Neurol.* 308, 555–575.
26. Joachim, C. L., Morris, J. H. and Selkoe, D. J. (1989) *Am. J. Pathol.* 135, 309–319.
27. Morgenstern, J. P. and Land, H. (1990) *Nucleic Acids Res.* 18, 3587.
28. Zhong, L. T., Man, S. P., Edwards, R. H., Bredesen, D. E. *Soc. Neurosci. Abstr.* 18, 44 1992; Zhong, L. T. et al., *Proc. Natl. Acad. Sci. USA,* 90 4533, 1993.
29. Chomezysnki, P. and Sacchi, N., *Anal. Biochem,* 162, 156 (1987).

What is claimed is:

1. A method for increasing the resistance of neural cells to B-amyloid peptide toxicity wherein said neural cells naturally express the $p75^{NTR}$, said method comprising the steps of:

providing a neural cell culture which comprises a plurality of neural cells which naturally express $p75^{NTR}$ and which have a low resistance to B-amyloid peptide toxicity;

treating said neural cell culture with a sufficient amount of a binding agent to bind said $p75^{NTR}$ which are expressed by said neural cells to form a modified neural cell culture which comprises neural cells wherein the $p75^{NTR}$ of said neural cells are bound to said binding agent; and exposing said modified neural cell culture to B-amyloid peptide wherein the resistance of said modified neural cell culture to B-amyloid peptide toxicity is higher than the resistance of said neural cell culture to B-amyloid peptide toxicity.

2. A method for increasing the resistance of neural cells to B-amyloid peptide toxicity according to claim 1 wherein said neural cells which naturally express the $p75^{NTR}$ are selected from the group consisting of basal forebrain cholinergic neurons, cortical neurons, hippocampal neurons, nucleus basalis neurons, or neurons in which $p75^{NTR}$ has been upregulated due to axotomy or other insult.

3. A method for increasing the resistance of neural cells to B-amyloid peptide toxicity according to claim 1 wherein said binding agent is selected from the group consisting of nerve growth factor, brain-derived neurotrophic factor (BDNF) neurotrophin-3 (NT-3), and neurotrophin-4/5 (NT-4/5).

4. A method for increasing the resistance of neural cells to B-amyloid peptide toxicity according to claim 1 wherein said neural cells are basal forebrain cholinergic neurons and said binding agent is nerve growth factor.

* * * * *